US011523840B2

(12) United States Patent
Yuan et al.

(10) Patent No.: US 11,523,840 B2
(45) Date of Patent: Dec. 13, 2022

(54) SURGICAL INSTRUMENT

(71) Applicant: Shanghai Microport Medbot (Group) Co., Ltd., Shanghai (CN)

(72) Inventors: Shuai Yuan, Shanghai (CN); Youkun Jiang, Shanghai (CN); Chao He, Shanghai (CN); Yuyuan He, Shanghai (CN)

(73) Assignee: SHANGHAI MICROPORT MEDBOT (GROUP) CO., LTD., Shanghai (CN)

( * ) Notice: Subject to any disclaimer, the term of this patent is extended or adjusted under 35 U.S.C. 154(b) by 196 days.

(21) Appl. No.: 16/768,222

(22) PCT Filed: Nov. 23, 2018

(86) PCT No.: PCT/CN2018/117102
§ 371 (c)(1),
(2) Date: May 29, 2020

(87) PCT Pub. No.: WO2019/105289
PCT Pub. Date: Jun. 6, 2019

(65) Prior Publication Data
US 2020/0289141 A1 Sep. 17, 2020

(30) Foreign Application Priority Data
Dec. 1, 2017 (CN) .......................... 201711252660.9

(51) Int. Cl.
*A61B 17/29* (2006.01)
*A61B 17/00* (2006.01)

(52) U.S. Cl.
CPC .... *A61B 17/29* (2013.01); *A61B 2017/00318* (2013.01); *A61B 2017/00477* (2013.01)

(58) Field of Classification Search
CPC .................. A61B 17/29; A61B 17/28; A61B 2017/00318; A61B 2017/00477; A61B 2017/003; A61B 2017/00323
See application file for complete search history.

(56) References Cited

U.S. PATENT DOCUMENTS

| 8,518,024 B2 | 8/2013 | Williams et al. |
| 2005/0096694 A1 | 5/2005 | Lee |

(Continued)

FOREIGN PATENT DOCUMENTS

| CN | 101040773 A | 9/2007 |
| CN | 102309363 A | 1/2012 |

(Continued)

*Primary Examiner* — Brooke Labranche
(74) *Attorney, Agent, or Firm* — Muncy, Geissler, Olds & Lowe, P.C.

(57) ABSTRACT

A surgical instrument (10), comprising: a surgical execution component (100), a linkage part (200), and a manipulation component (300), the distal end of the linkage part (200) being connected to the surgical execution component (100) and the proximal end of the linkage part (200) being connected to the manipulation component (300). The surgical instrument (10) uses the linkage part (200) having two rotational degrees of freedom, such that when the manipulation component (300) drives, by means of the linkage part (200), the surgical execution component (100) to rotate at a fifth rotational degree of freedom (R5) and/or a sixth rotational degree of freedom (R6), the swing directions of the surgical execution component (100) and the manipulation component (300) at a first rotational degree of freedom (R1) and a second rotational degree of freedom (R2) are consistent. Therefore, the surgical instruction (10) implements technical effects of improving the moving direction accuracy of the surgical execution component (100), improving the accuracy of the action of the surgical instruction (10), and facilitating surgical operations.

19 Claims, 5 Drawing Sheets

(56) References Cited

U.S. PATENT DOCUMENTS

| | | | |
|---|---|---|---|
| 2007/0221700 A1* | 9/2007 | Ortiz | A61B 34/72 |
| | | | 227/175.1 |
| 2008/0046000 A1* | 2/2008 | Lee | A61B 17/29 |
| | | | 606/205 |
| 2013/0144306 A1 | 6/2013 | Stefanchik et al. | |
| 2016/0192915 A1 | 7/2016 | Papenfuss et al. | |

FOREIGN PATENT DOCUMENTS

| | | |
|---|---|---|
| CN | 103251458 A | 8/2013 |
| CN | 104970840 A | 10/2015 |
| CN | 105592801 A | 5/2016 |
| CN | 105943095 A | 9/2016 |
| CN | 106551716 A | 4/2017 |
| CN | 107072684 A | 8/2017 |
| CN | 107080588 A | 8/2017 |
| CN | 107260307 A | 10/2017 |
| CN | 107928790 A | 4/2018 |
| CN | 108013906 A | 5/2018 |
| CN | 108030518 A | 5/2018 |
| WO | WO-2011-1014711 A1 | 2/2011 |

\* cited by examiner

SURGICAL INSTRUMENT

TECHNICAL FIELD

The present disclosure relates to the field of medical instruments and, in particular, to a surgical instrument.

BACKGROUND

In minimally invasive surgery, especially laparoscopic or endoscopic surgery, a tiny cut is made, which usually requires the use of minimally invasive surgical instruments for achieving a better treatment result with reduced damages to other tissues. During the operation, unnecessary movements of an existing minimally invasive surgical instrument are easily transmitted to an end effector of the surgical instrument, thus affecting the surgical instrument's movements.

Chinese Patent Application No. CN107072684A proposes an attachment apparatus for a remote access tool, which includes a cuff configured to attach to the user's forearm and a coupling joint configured to connect the cuff to a frame so that the cuff has 1 to 4 moving degrees of freedom relative to the frame.

Chinese Patent Application No. CN105592801A proposes a control unit for a medical device, which includes: a palm interface engageable by a palm of a hand; a restraint capable of elastically deforming to apply a restraining force to the back of the hand; and a finger interface engageable by one or more fingers of said hand.

Chinese Patent Applications No. CN107080588A and No. CN107260307A propose a cable-driven control device of the minimally invasive surgery robot and a cable-driven clamping device of the minimally invasive surgery robot.

SUMMARY

In view of the above, it is necessary to provide an improved surgical instrument against the problem such as unnecessary movements being transmitted to the end effector during operations of the existing surgical instruments.

Some embodiments of the present disclosure provide a surgical instrument comprising an surgical effector assembly, a flexible snake-like assembly, a linkage member and a manipulation assembly, the flexible snake-like assembly having a distal end connected to the surgical effector assembly and a proximal end connected to a distal end of the linkage member, the linkage member having a proximal end connected to the manipulation assembly, the linkage member being able to rotate about a first axis and a second axis, the flexible snake-like assembly being able to rotate about a fifth axis and a sixth axis.

When the manipulation assembly drives the linkage member to rotate about the first axis, the flexible snake-like assembly is driven to rotate about the fifth axis, a direction of the rotation of the flexible snake-like assembly about the fifth axis being the same as a direction of the rotation of the linkage member about the first axis.

When the manipulation assembly drives the linkage member to rotate about the second axis, the flexible snake-like assembly is driven to rotate about the sixth axis, a direction of the rotation of the flexible snake-like assembly about the sixth axis being the same as a direction of the rotation of the linkage member about the second axis.

In the above surgical instrument, through the linkage member with two rotational degrees of freedom, when the manipulation assembly drives the surgical effector assembly to rotate in the fifth and/or sixth rotational degree of freedom(s), the swing directions of the surgical effector assembly in the fifth and/or sixth rotational degree(s) of freedom is in consistent with the swing directions of the manipulation assembly in the first and second rotational degrees of freedom. Therefore, the surgical instrument is provided with an improved directional accuracy of movements of the surgical effector assembly, an enhanced action accuracy of the surgical instrument and facilitated surgical operations.

In the some embodiments, the linkage member comprises a spherical hinge, the spherical hinge comprising a sphere and a spherical shell that have a common spherical center, the spherical hinge being restricted from self-rotating about a restricting axis of the spherical shell.

In the some embodiments, the linkage member further comprises a limiting pin that is arranged on a surface of the sphere, and has a central axis extending through the common spherical center, the central axis of the limiting pin forming the first axis;

wherein a guiding groove is formed on an inner surface of the spherical shell, a extending direction of which is a circumference direction about the spherical center, the limiting pin inserted in the guiding groove to cause the limiting pin being circumferentially movable along the extending direction of the guiding groove, the guiding groove having side walls configured to prevent the limiting pin from rotating about the axis of the spherical shell, an axis about which the limiting pin moves circumferentially along the extending direction of the guiding groove forming the second axis; and wherein any two of the axis of the spherical shell, the central axis of the limiting pin and the axis about which the limiting pin moves circumferentially along the extending direction of the guiding groove are perpendicular to each other.

In the some embodiments, the surgical instrument further comprises a hand-held portion and a connecting portion that are sequentially connected, the hand-held portion having a proximal end connected to the linkage member, the connecting portion having a distal end connected to the flexible snake-like assembly.

In the some embodiments, the hand-held portion comprises an arc-shaped body having a proximal end provided with a proximal holder and a distal end provided with a distal holder, the proximal holder having a distal end fixedly connected to the linkage member, the distal holder having a distal end fixedly connected to the connecting portion.

In some embodiments, the surgical instrument further comprises a flexible transmission mechanism having a proximal end connected to the linkage member and a distal end connected to the flexible snake-like assembly, where a position at which the flexible transmission mechanism is connected to the linkage member and a position at which the flexible transmission mechanism is connected to the flexible snake-like assembly are arranged in an opposite manner.

In some embodiments, the surgical instrument further comprises a hand-held portion and a connecting portion that are sequentially connected, the hand-held portion having a proximal end connected to the linkage member, the connecting portion having a distal end connected to the flexible snake-like assembly, where the hand-held is provided with a second passage and connecting portions is provided with a first passage, through which the flexible transmission mechanism passes.

In the some embodiments, the surgical instrument further comprises at least one steering wheel arranged within the second passage of the hand-held portion, through which the flexible transmission mechanism changes extending direction thereof.

In the some embodiments, the surgical effector assembly comprises a support portion and an end effector, the support portion connected to the flexible snake-like assembly, the end effector being movable relative to the support portion.

In the some embodiments, the surgical instrument further comprises an opening/closing transmission assembly having a distal end connected to the end effector and a proximal end connected to the manipulation assembly, wherein the manipulation assembly causes the end effector to rotate relative to the support portion by means of the opening/closing transmission assembly.

In the some embodiments, the manipulation assembly comprises a gripping portion and at least one control segment, the gripping portion connected to the spherical hinge, the control segment having a proximal end rotatably connected to the gripping portion, and the proximal end of the opening/closing transmission assembly is connected to the control segment, so that a rotation of the control segment relative to the gripping portion drives the opening/closing transmission assembly, which in turn drives the end effector to rotate relative to the support portion.

In the some embodiments, the end effector may comprise a first jaw and a second jaw, which are able to rotate relative to each other, each of the first and second jaws rotatably connected to the support portion.

In some embodiments, the opening/closing transmission assembly comprises a transmission shaft, a first opening/closing coupling parts and a second opening/closing coupling parts, the first opening/closing coupling parts having a proximal end connected to the at least one control segment and a distal end connected to the transmission shaft, the second opening/closing coupling parts having a distal end connected to each of the first and second jaws and a proximal end connected to the transmission shaft, and when the control segment is rotated relative to the gripping portion, the control segment drives the first opening/closing coupling parts to move, which causes the first opening/closing coupling parts to drive the transmission shaft to move, so that the transmission shaft drives the second opening/closing coupling parts to move, which causes the second opening/closing coupling parts to drive the first and second jaws to rotate relative to each other.

In some embodiments, the manipulation assembly comprises a first control segment and a second control segment, the first opening/closing coupling parts comprising a first link rod and a second link rod, the first link rod having a proximal end rotatably connected to a distal end of the first control segment, the second link rod having a proximal end rotatably connected to a distal end of the second control segment, each of the first and second link rods having a distal end rotatably connected to the transmission shaft, and when the first and second control segments rotate relative to each other, the first and second control segments are able to respectively drive the first and second link rods to rotate relative to each other, so that the first and second link rods drives the transmission shaft to move along an extending direction of the transmission shaft.

In the some embodiments, the second opening/closing coupling parts comprises a third link rod and a fourth link rod, the third link rod having a distal end rotatably connected to a proximal end of the first jaw, the fourth link rod having a distal end rotatably connected to a proximal end of the second jaw, each of the third and fourth link rods having a proximal end rotatably connected to the transmission shaft, and when the transmission shaft move towards an extending direction thereof, the transmission shaft drives the third and fourth link rods to rotate relative to each other, so that the third and fourth link rods respectively drives the first and second jaws to rotate relative to each other.

In the some embodiments, the opening/closing transmission assembly further comprises a first elastic member disposed between the first link rod and the second link rod.

In the some embodiments, the opening/closing transmission assembly further comprises a second elastic member disposed between the third and fourth link rods.

In the some embodiments, the opening/closing transmission assembly further comprises at least one third elastic member disposed between the control segment and the gripping portion.

In some embodiments, the opening/closing transmission assembly further comprises a fourth elastic member disposed between the first and second jaws.

In some embodiments, the surgical instrument further comprises a first locking member. The locking member is connected to the spherical hinge and configured to allow or disallow a rotation of the spherical hinge about the first and second axes; and/or the locking member is connected to the manipulation assembly and configured to lock or unlock driving of the spherical hinge by the manipulation assembly so as to allow or disallow the rotation of the spherical hinge about the first and second axes.

In some embodiments, an axis of the spherical shell is provided with a third passage and the sphere is provided with a fourth passage, the third passage having a central axis collinear with a central axis of the fourth passage, the transmission shaft passing through the third and fourth passages. The spherical shell is located between the gripping portion and the sphere. The sphere is provided with conical cavity thereon. The conical cavity is in communication with the fourth passage and has a central axis coincident with the central axis of the fourth passage. The conical cavity is arranged at a side of the sphere close to the manipulation assembly.

In some embodiments, the manipulation assembly is rotatable about the central axis of the third passage, so that the manipulation assembly drives the transmission shaft to rotate, which in turn causes the transmission shaft to drive the surgical effector assembly to self-rotate.

In some embodiments, the surgical instrument further comprises a second locking member connected to the manipulation assembly and configured to allow or disallow the manipulation assembly to rotate about the central axis of the first third passage.

DETAILED DESCRIPTION

Specific embodiments of the present disclosure is described in detail with reference to the accompanying drawings to make the above objects, features and advantages of the present disclosure more apparent and readily understood.

Figure 1:
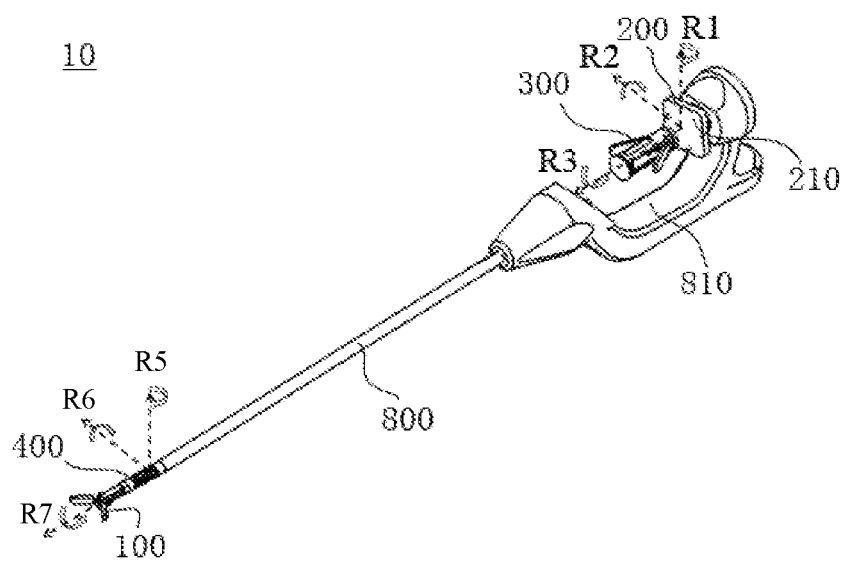
FIG. 1 is a schematic diagram of a surgical instrument.

Referring to FIG. 1, a surgical instrument 10 according to some embodiments includes a surgical effector assembly 100, a linkage member 200, a manipulation assembly 300 and a flexible snake-like assembly 400. The linkage member 200 is connected to the manipulation assembly 300, and the linkage member 200 is able to rotate about a first axis and a second axis and thus has a first rotational degree of freedom R1 and a second rotational degree of freedom R2. The flexible snake-like assembly 400 is connected to the surgical effector assembly 100, and the flexible snake-like assembly 400 is able to rotate about a fifth axis and a sixth axis and thus has a fifth rotational degree of freedom R5 and a sixth rotational degree of freedom R6. When the manipulation assembly 300 drives the linkage member 200 to rotate about the first axis, the flexible snake-like assembly 400 is configured to be driven to rotate about the fifth axis, and the rotation direction of the flexible snake-like assembly 400 in fifth rotational degree of freedom R5 is the same as the rotation direction of the linkage member 200 in first rotational degree of freedom R1. When the manipulation assembly 300 drives the linkage member 200 to rotate about the second axis, the flexible snake-like assembly 400 is configured to be driven to rotate about the sixth axis, and the rotation direction of the flexible snake-like assembly 400 in sixth rotational degree of freedom R6 is the same as the rotation direction of the linkage member 200 in second rotational degree of freedom R2. The directions of the first, second, fifth and sixth rotational degrees of freedom R1, R2, R5 and R6 are as shown in FIG. 1. Preferably, the first and second axes are perpendicular to each other and the fifth and sixth axes are perpendicular to each other, with the first axis being parallel to the fifth axis. The surgical effector assembly 100 may be implemented as a surgical effector, such as a surgical forceps, a surgical scissors, a surgical gripper or the like, and is configured to perform the operations such as gripping in the surgery.

Further, the surgical effector assembly 100 is connected to the flexible snake-like assembly 400 with two rotational degrees of freedom. Therefore, when the manipulation assembly 300 drives the linkage member 200 to rotate about the first axis, the flexible snake-like assembly 400 is driven to rotate about the fifth axis, which in turn causes the surgical effector assembly 100 to rotate about the fifth axis and thus imparts a rotational degree of freedom R5' to the surgical effector assembly 100; and when the manipulation assembly 300 drives the linkage member 200 to rotate about the second axis, the flexible snake-like assembly 400 is driven to rotate about the sixth axis, which in turn causes the surgical effector assembly 100 to rotate about the sixth axis and thus imparts a rotational degree of freedom R6' to the surgical effector assembly 100. And, the manipulation assembly 300 has a free end oriented towards the same direction as a free end of the surgical effector assembly 100, and swing directions of the flexible snake-like assembly 400 at the fifth and sixth rotational degrees of freedom R5, R6 is consistent with that of the linkage member 200 at the first and second rotational degrees of freedom R1, R2, while the swing directions of manipulation assembly 300 is consistent with that of the surgical effector assembly 100, so the surgical instrument 10 provides the advantages of an improved directional accuracy of movements of the surgical effector assembly 100, an enhanced operation accuracy of the surgical instrument 10, thereby facilitating surgical operations.

Figure 2:
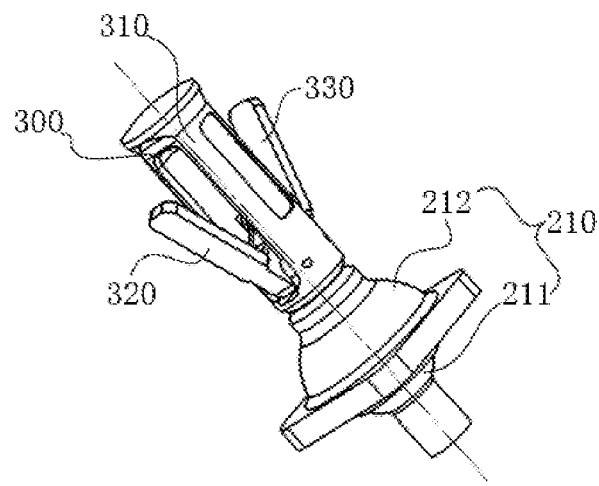
FIG. 2 schematically illustrates how a manipulation assembly and a spherical hinge are connected to each other in the surgical instrument of FIG. 1.
Figure 3:
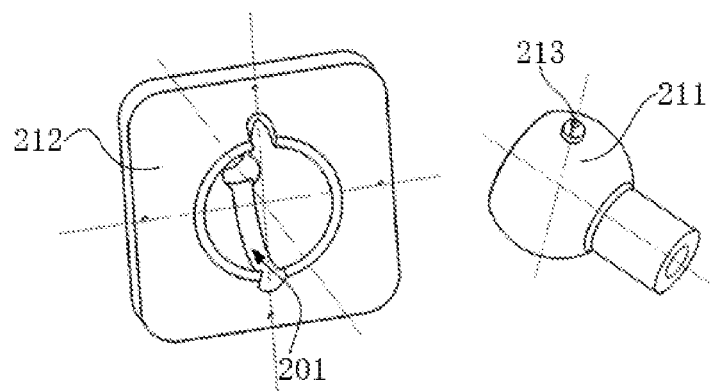
FIG. 3 is a schematic exploded view of the spherical shell and a sphere of the surgical instrument of FIG. 1.

Referring to FIG. 2 and FIG. 3, in some embodiments, the linkage member 200 includes a spherical hinge 210 including a sphere 211 with an extension and a spherical shell 212. The sphere 211 and the spherical shell 212 have a common spherical center. An axis of the extension on the sphere 211 extends through the spherical center. The linkage member 200 has two rotational degrees of freedom, whereas the common spherical hinge inherently has three rotational degrees of freedom. Therefore, the third rotational degree of freedom of the spherical hinge 210 is required to be restricted to make the spherical hinge 210 having only two rotational degrees of freedom. In the embodiments, the spherical hinge 210 is restricted from rotating about the axis on which the extension is located. The use of the spherical hinge 210 to form the linkage member 200 with two rotational degrees of freedom can facilitate control of rotation, and provide an ease use.

Specifically, referring to FIG. 3, in some embodiments, the spherical hinge is restricted from rotating about a restricting axis of the spherical shell (i.e., the axis on which the extension of the sphere 211 is located in an initial state) through the following method. The linkage member 200 further comprises a limiting pin 213 on a surface of the sphere 211 and the central axis of the limiting pin 213 passes through the common spherical center. A guiding groove 201 is formed on an inner surface of the spherical shell 212 and the extending direction of the guiding groove 201 is a circumference direction about the spherical center. The limiting pin 213 is received into the guiding groove 201 so that the limiting pin 213 is able to move circumferentially along the extending direction of the guiding groove 201. Side walls of the guiding groove are configured to prevent the limiting pin 213 from rotating about the axis of the spherical shell. i.e., rotating about the axis on which the extension of the sphere 211 in the initial state is located. The axis of the spherical shell, the central axis of the limiting pin 213 (i.e., the first axis) and the axis about which the limiting pin 213 moves circumferentially along the extending direction of the guiding groove 201 (i.e., the second axis) are configured such that any two of them are perpendicular to each other.

More specifically, the limiting pin 213 is provided on the surface of the sphere 211, and the guiding groove 201 is disposed on the inner surface of the spherical shell 212, which surrounds the spherical center, the guiding groove 201 being situated in a plane defined by the restricting axis of the spherical shell and the central axis of the limiting pin 213. In addition, since any two of the axis of the spherical shell, the central axis of the limiting pin 213 and the axis about which the limiting pin 213 moves circumferentially along the extension of the guiding groove 201 are perpendicular to each other, the limiting pin 213 is able to move circumferentially along the extending direction of the guiding groove 201 and rotatable about the central axis of the limiting pin 213, while being prevented by the side walls of the guiding groove from rotating about the axis at which the extension of the sphere 211 is located. As a result, the sphere 211 only has two rotational degrees of freedom, thus allowing the manipulation assembly 300 to drive the surgical effector assembly 100 to rotate about the fifth and sixth axes by means of the spherical hinge 210.

Figure 4:
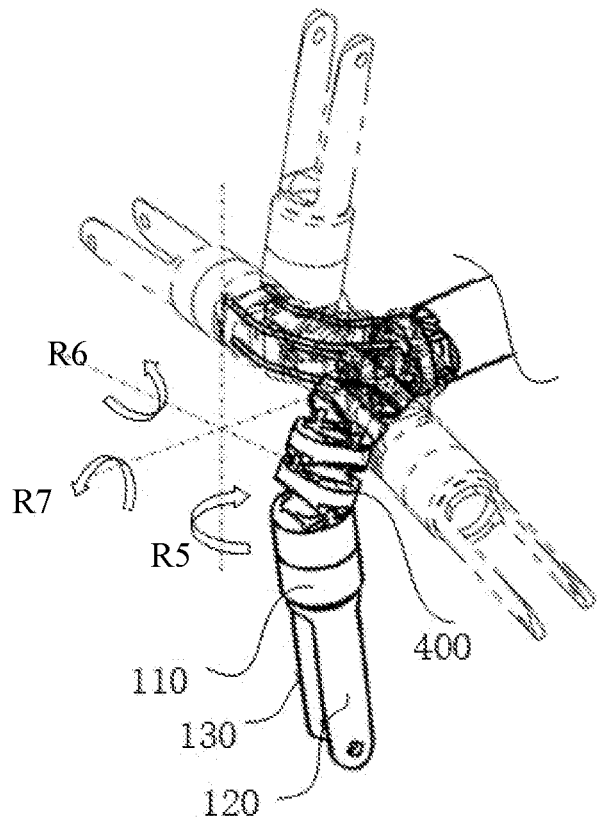
FIG. 4 is a schematic diagram illustrating how a flexible snake-like assembly of the surgical instrument of FIG. 1 swings in the first and second rotational degrees of freedom.

Referring to FIG. 4, due to the flexible nature of the flexible snake-like assembly 400, when the linkage member 200 drives the flexible snake-like assembly 400 to move, the flexible snake-like assembly 400 can in turn cause the surgical effector assembly 100 to rotate about the fifth and sixth axes to form two rotational degrees of freedom R5, R6. Further, the surgical effector assembly 100 is able to self-rotate (revolve on its own axis) to form a self-rotational degree of freedom R7. As such, the surgical effector assembly 100 has three degrees of freedom, thereby allowing flexible changes of the postures of the surgical effector assembly 100 to meet various gripping posture needs in a narrow space and improve convenience of surgical operations.

Figure 5:
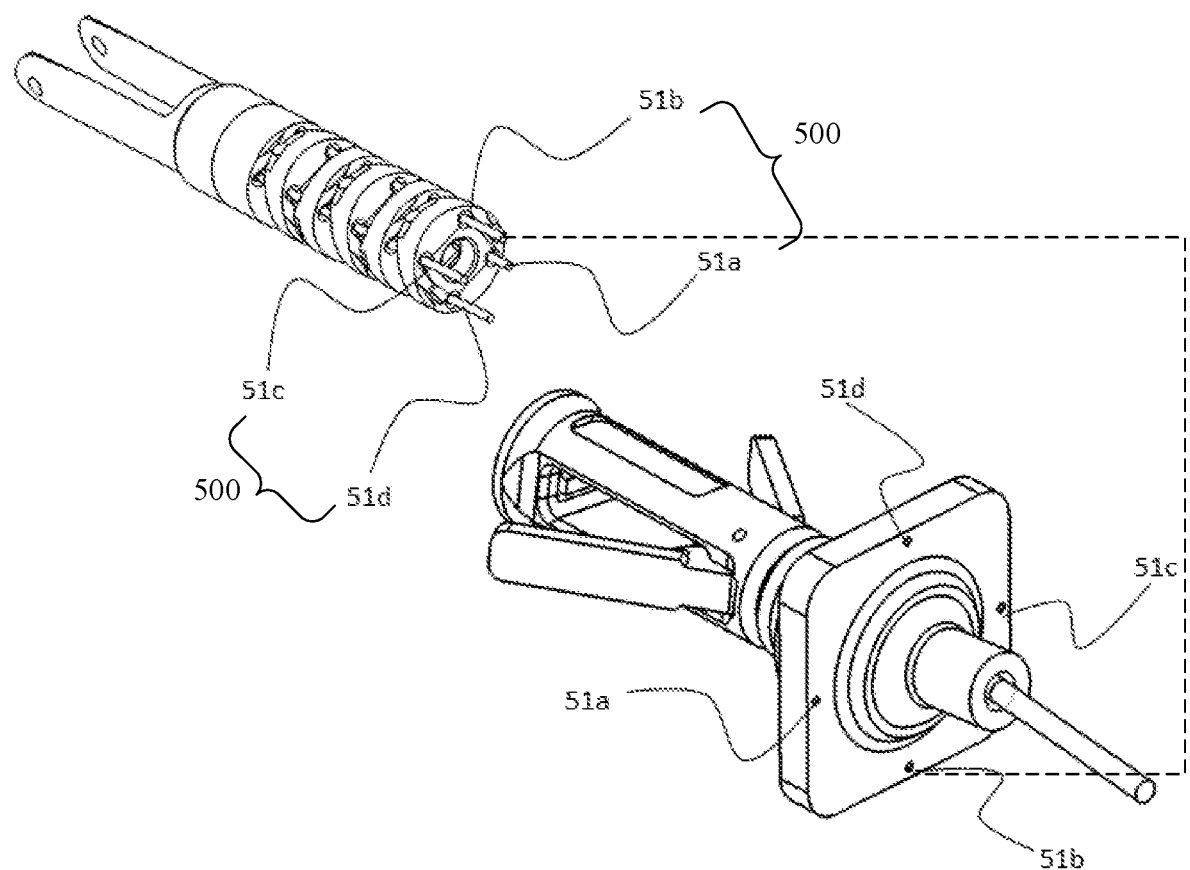
FIG. 5 schematically illustrates how a first flexible wire transmission assembly and a second flexible wire transmission assembly are connected to the manipulation assembly and the flexible snake-like assembly of the surgical instrument of FIG. 1.

In order to ensure that the manipulation assembly 300 and the surgical effector assembly 100 have a same movement direction when they have a same orientation direction, referring to FIG. 5, in some embodiments, the surgical instrument 10 further includes a flexible transmission mechanism 500 having a proximal end connected to the linkage member 200 and a distal end connected to the flexible snake-like assembly 400. The position where the flexible transmission structure 500 is connected to the linkage member 200 and the position where the flexible transmission structure 500 is connected to the flexible serpentine mechanism 400 are arranged in an opposite manner Here, "arranged in an opposite manner" refers to being arranged in the following manner. For example, if the position where the proximal end of the flexible transmission mechanism 500 is connected to the flexible snake-like assembly 400 is located at an upper side, then the position where the distal end of the flexible transmission mechanism 500 is connected to the linkage member 200 is located at a lower side; or if the position where the proximal end of the flexible transmission mechanism 500 is connected to the flexible snake-like assembly 400 is located on a left side, then the position where the distal end of the flexible transmission mechanism 500 is connected to the linkage member 200 is located on a right side.

In some embodiments, as shown in FIG. 5, the linkage member 200 includes the spherical hinge 210 including the sphere 211 and the spherical shell 212, and the flexible transmission mechanism 500 includes four flexible parts 51a, 51b, 51c, 51d. In this case, the flexible snake-like assembly 400 includes four connecting points, among which the upper and lower connecting points are used to control the flexible snake-like assembly 400 to swing up and down; and the left and right connecting points are used to control the flexible snake-like assembly 400 to rotate left and right.

Accordingly, the spherical shell 212 also includes four connecting points, to which the four flexible parts 51a, 51b, 51c, 51d are respectively connected from the left side in a counterclockwise manner. The snake-like joint 41 also includes four connecting points, to which the other ends of the four flexible parts 51c, 51d, 51a, 51b are respectively connected from the left side in a counterclockwise manner. Taking 51b in FIG. 5 as an example, where the junction positions at both ends of 51b are indicated by dotted lines. Further, the first axis passes through the connecting points of the flexible parts 51b, 51d to the spherical shell 212, and the second axis passes through the connecting points of the flexible parts 51a, 51c to the spherical shell 212. Correspondingly, the fifth axis passes through the connecting points of the flexible parts 51b, 51d to the flexible snake-like assembly 400, and the sixth axis passes through the connecting points of the flexible parts 51a, 51c to the flexible snake-like assembly 400.

Connections between the above components allow the flexible snake-like assembly 400 to rotate about both the fifth and sixth axes while enabling the flexible snake-like assembly 400 to move, under the control of the manipulation assembly 300, towards the same direction as the manipulation assembly 300. In other words, the flexible snake-like assembly 400 and the manipulation assembly 300 consistent movement directions. This can prevent user's operations from being transmitted back to the end effector assembly, which may affect the instrument's movement accuracy. It should be appreciated by those skilled in the art that the number of attachment points on the flexible snake-like assembly 400/spherical shell 212 is not limited to 4 and may be 6, 8 or the like. An increased number of such attachment points can obtain an increased control accuracy of the flexible snake-like assembly 400/spherical shell 212.

Referring to FIG. 1, in some embodiments, the surgical instrument 10 further includes a hand-held portion 810 and a connecting portion 800 that are sequentially connected. The arrangement of hand-held portion 810 allows the surgical instrument 10 to be easily held by hand in using, so as to improve the convenience of operation. The connecting portion 800 is configured to support the surgical effector assembly and the flexible snake-like assembly. Further, the connecting portion 800 is provided with a first passage, through which the flexible transmission mechanism 500 passes. The connecting portion 800 has a proximal end connected to the hand-held portion 810 and a distal end connected to the flexible snake-like assembly 400. Specifically, the flexible transmission mechanism 500 passes through the first passage of the connecting portion 800, so that the flexible transmission mechanism 500 can be protected by the connecting portion 800 and free from interferences and damages outside the cavity of the connection portion 800, thereby enabling to improve action accuracy of the surgical instrument 10.

Figure 6:
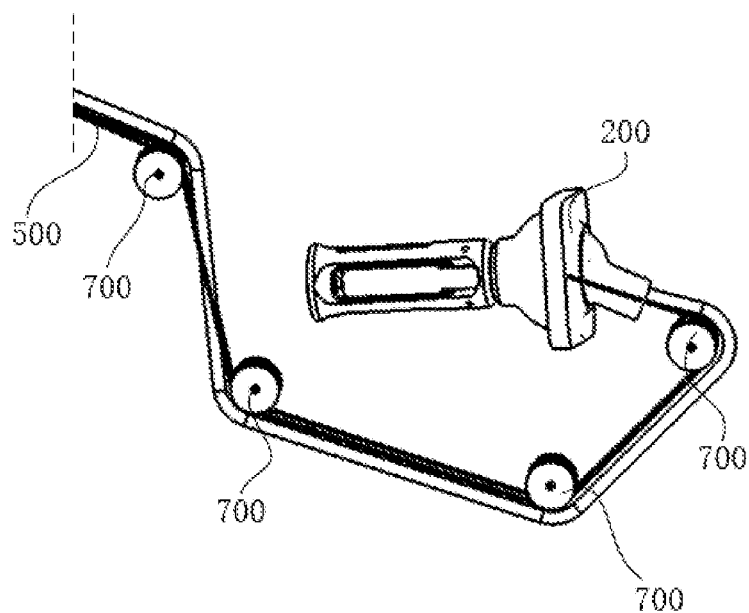
FIG. 6 schematically illustrates how the first flexible wire transmission assembly is connected to steering wheel(s) and a linkage member in the surgical instrument of FIG. 1.

Referring to FIG. 1, in some embodiments, the hand-held portion 810 includes an arc-shaped body. The proximal end of the arc-shaped body is provided with a proximal holder and the distal end of the arc-shaped body is provided with a distal holder. The specific curve shape of the arc-shaped body is not limited and may adopt any suitable ergonomic design. A distal end of the distal holder is fixedly connected to the connecting portion 800. A distal end of the proximal holder is fixedly connected to linkage member 200 for providing the linkage member 200 with support and facilitating the hand-holding. Further, the hand-held portion 810 is provided with a second passage, for the flexible transmission mechanism 500 to pass through. In this case, referring to FIG. 6, the surgical instrument 10 further includes a steering wheel 700. One steering wheel 700 may be provided, or more steering wheels 700 may be provided. The steering wheel is arranged within the second passage of the hand-held portion 810, so that the flexible transmission mechanism 500 can change its extending direction in the second passage of the curved hand-held portion 810 by means of the steering of steering wheel 700 as flexible transmission mechanism 500 passes through the second passage of the hand-held portion 810.

Figure 7:
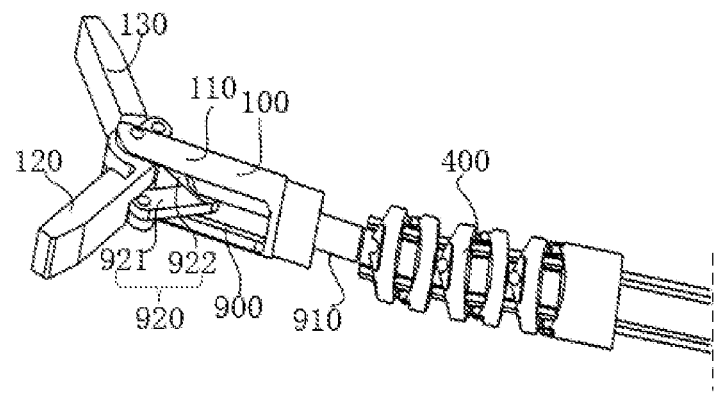
FIG. 7 schematically illustrates how a surgical effector assembly, an opening/closing transmission assembly and the flexible snake-like assembly are connected to one another in the surgical instrument of FIG. 1.

The surgical effector assembly 100 includes a support portion 110 and an end effector. The support portion 110 is connected to the flexible snake-like assembly 400 and the end effector is able to move, for example, translate or rotate relative to the support portion. Referring to FIG. 7, in some embodiments, the end effector includes a first jaw 120 and a second jaw 130, the first jaw 120 having a proximal end rotatably connected to the support portion 110 and a distal end being a free end, the second jaw 130 having a proximal end connected to the support portion 110 and a free end being a free end. This arrangement can offer the end effector an opening/closing degree of freedom. The surgical instrument 10 furthers include an opening/closing transmission assembly 900 configured to drive the end effector to move. Specifically, in the embodiments of FIG. 7, the opening/closing transmission assembly 900 has a distal end connected to the first jaw 120 and a proximal end connected to the manipulation assembly 300. The opening/closing transmission assembly 900 is driven by the operation of the operating assembly 300 to move, which in turn causes the first jaw 120 and the second jaw 130 to rotate relative to the support portion 110 under the transmission action of opening/closing transmission assembly 900. In this way, the first jaw 120 and the second jaw 130 are able to be relatively opened or closed through the relative rotation, enabling to perform operations of gripping, clamping or the like during the operation.

In addition, the second jaw 130 may be fixedly connected to the support portion 110. In this case, the opening/closing transmission assembly 900 is driven by the operation of the operating assembly 300 to move, which in turn causes the first jaw 120 to move under the transmission action of opening/closing transmission assembly 900. In this way, the first jaw 120 and the second jaw 130 are able to be relatively opened or closed through the relative rotation, enabling to perform operations of gripping, clamping or the like during the operation.

Alternatively, the second jaw 130 may also be rotatably connected to the support portion 110. In this case, the distal end of the opening/closing transmission assembly 900 may be also connected to the second jaw 120. As such, the opening/closing transmission assembly 900 is driven by the operation of the manipulation assembly 300 to move, which in turn causes the first jaw 120 and the second jaw 130 to move under the transmission action of opening/closing transmission assembly 900, so that relative rotation between the first jaw 120 and the second jaw 130 can be obtained. In this way, the first jaw 120 and the second jaw 130 are able to be relatively opened or closed through the relative rotation, enabling to perform operations of gripping, clamping or the like in the surgery.

Referring to FIG. 2, in some embodiments, the manipulation assembly 300 includes a gripping portion 310 and a first control segment 320. The gripping portion 310 is connected to the spherical hinge 210. One end of the first control segment 320 is rotatably connected to the gripping portion 310, while the other end thereof is a free end. This offers the proximal end of the surgical instrument 10 a fourth degree of freedom R4. The proximal end of the opening/closing transmission assembly 900 is connected to the first control segment 320, and the first control segment 320 can be controlled to rotate relative to the gripping portion 310, so that the opening/closing transmission assembly 900 is driven to move. Then, the first jaw 120 is driven to move to obtain relative rotation between the first jaw 120 and the second jaw 130. As a result, the first jaw 120 and the second jaw 130 are able to be relatively opened or closed through the relative rotation, enabling to perform operations of gripping, clamping or the like during the operation.

The manipulation assembly 300 further includes a second control segment 330, which has one end rotatably connected to the gripping portion 310 and the other end being a free end. In this case, the proximal end of the opening/closing transmission assembly 900 is also connected to the second control segment 330. Likewise, the second control segment 330 can be controlled to rotate relative to the gripping portion 310, which in turn drives the opening/closing transmission assembly 900 to move, thereby enabling relative rotation between the first jaw 120 and second jaw 130.

Specifically, the first control segment 320 is driven to rotate relative to the gripping portion 310 and/or the second control segment 330 is driven to rotate relative to the gripping portion 310, so that the opening/closing transmission assembly 900 is driven to move, which in turn causes the first jaw 120 and/or the second jaw 130 to move under the transmission action of opening/closing transmission assembly 900. In this way, the first jaw 120 and the second jaw 130 are able to be relatively opened or closed through the relative rotation between the first jaw 120 and the second jaw 130, enabling to perform operations of gripping, clamping or the like during the operation.

Further, in order to facilitate the manipulations of the first and second control segments 320, 330, the first and second control segments 320, 330 may be provided thereon with respective finger cuffs 340 that allow the insertion of fingers therethrough.

Further, the first and second control segments 320, 330 may be symmetrically disposed on opposing sides of the gripping portion 310, in order to facilitate manipulations.

Figure 8:
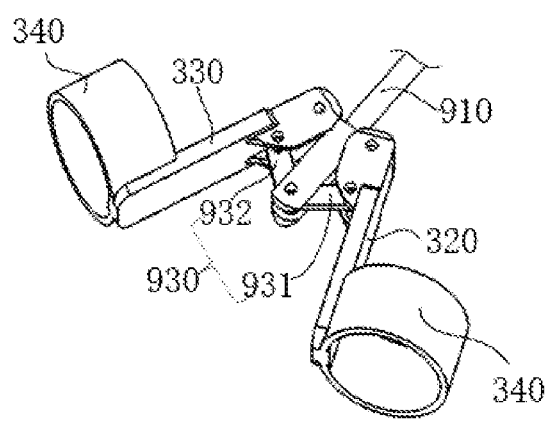
FIG. 8 schematically illustrates how the manipulation assembly and opening/closing transmission assembly are connected to each other in the surgical instrument of FIG. 1.

Referring to FIG. 7 and FIG. 8 (in which, the gripping portion 310 is omitted for the sake of simplicity), in some embodiments, the opening/closing transmission assembly 900 includes a transmission shaft 910, a first opening/closing coupling parts 930 and a second opening/closing coupling parts 920. In particular, the transmission shaft 910 may be a nickel-titanium alloy wire, a steel wire, a soft shaft or the like. One end of the first opening/closing coupling parts 930 is connected to each of the first and second control segments 320, 330. The other end of the first opening/closing coupling parts 930 is connected to the proximal end of the transmission shaft 910. One end of the second opening/closing coupling parts 920 is connected to each of the first and second jaws 120, 130. The other end of second opening/closing coupling parts 920 is connected to a distal end of the transmission shaft 910. When the first control segment 320 rotates relative to the gripping portion 310 and the second segment 330 rotates relative to the gripping portion 310, the first and second segments 320, 330 can drive the first opening/closing coupling parts 930 to move, so that the transmission shaft 910 is driven by the first opening/closing coupling parts 930 to move. In turn, the transmission shaft 910 drives the second opening/closing coupling assembly 920 to move, thus causing the first and second jaws 120, 130 to rotate relative to each other under the driving of the second opening/closing coupling parts 920. As a result, the first jaw 120 and the second jaw 130 are able to be relatively opened or closed through the relative rotation between the first jaw 120 and the second jaw 130, enabling to perform operations of gripping, clamping or the like during the operation.

In some embodiments, the first opening/closing coupling parts 930 includes a first link rod 931 and a second link rod 932, the first link rod 931 having a proximal end rotatably connected to the distal end of the first control segment 320, the second link rod 932 having a proximal end rotatably connected to the distal end of the second control segment 330. Each of distal ends of the first and second link rods 931, 932 is rotatably connected to the transmission shaft 910. When the first and second control segments 320, 330 rotate relatively, the first and second link rods 931, 932 can be driven to rotate relatively by the first and second control segments 320, 330, which causes the proximal end of the transmission shaft 910 to move towards the extending direction of the transmission shaft 910 under the driving of the first and second link rods 931, 932, so that the second opening/closing coupling parts 920 is driven by the transmission shaft 910 to move. Further, the second opening/closing coupling parts 920 drives the first and second jaws 120, 130 to rotate relatively. As a result, the first jaw 120 and the second jaw 130 are able to be relatively opened or closed through the relative rotation between the first jaw 120 and the second jaw 130, enabling to perform operations of gripping, clamping or the like during the operation.

In some embodiments, the second opening/closing coupling parts 920 includes a third link rod 921 and a fourth link rod 922, the third link rod 921 having a distal end rotatably connected to the proximal end of the first jaw 120, the fourth link rod 922 having a distal end rotatably connected to the proximal end of the second jaw 130. Each of proximal ends of the third and fourth link rods 921, 922 is rotatably connected to the transmission shaft 910. When the transmission shaft 910 moves along its extending direction, the transmission shaft 910 is able to drive the third and fourth link rods 921, 922 to rotate relatively, which in turn causes the first and second jaws 120, 130 to rotate relatively under the driving of the third and fourth link rods 921, 922. As a result, the first jaw 120 and the second jaw 130 are able to be relatively opened or closed through the relative rotation between the first jaw 120 and the second jaw 130, enabling to perform operations of gripping, clamping or the like during the operation.

In some embodiments, the opening/closing transmission assembly 900 further includes a first elastic member (not shown). The first elastic member may be a compression spring or the like. The first elastic member is disposed between the first and second link rods 931, 932, so that a first spring force from the first elastic member enables relative rotation between the first and second link rods 931, 932. Due to the first spring force from the first elastic member, the first and second link rods 931, 932 can be in a relatively open configuration, which enables the first and second control segments 320, 330 to be driven by the he first and second link rods 931, 932 respectively, so that the first and second control segments 320, 330 are in a relatively open configuration and the first and second jaws 120, 130 are in a relatively open configuration. In use of the surgical instrument 10, the first and second jaws 120, 130 are relatively closed through manipulation, and respectively drive the first and second link rods 931, 932 to overcome the first spring force from first elastic member to make the first and second link rods 931, 932 relatively closed. Further, the first and second link rods 931, 932 drive the transmission shaft 910, and the transmission shaft 910 thus drives the third and fourth link rods 921, 922 to close relatively, which causes the first and second jaws 120, 130 to close relatively.

Likewise, in some embodiments, the opening/closing transmission assembly 900 further includes a second elastic member (not shown). The second elastic member may be a compression spring or the like. The second elastic member is disposed between the third and fourth link rods 921, 922, so that a second spring force from the second elastic member enables relative rotation between the third and fourth link rods 921, 922. Due to the second spring force from the second elastic members, the third and fourth link rods 921, 922 can be in a relatively open configuration, which enables the first and second jaws 120, 130 to be driven by the third and fourth link rods 921, 922 respectively, and the first and second jaws 120, 130 are in a relatively open configuration. In use of the surgical instrument 10, the first and second control segments 320, 330 are relatively closed through manipulation, and thus the first and second link rods 931, 932 drive the transmission shaft 910. Further, the transmission shaft 910 drives the third and fourth link rods 921, 922 to overcome the second spring force from second elastic member to make the third and fourth link rods 921, 922 relatively closed, which in turn cause the first and second jaws 120, 130 to close relatively.

In some embodiments, the opening/closing transmission assembly 900 further includes third elastic members (not shown). The third elastic member may be a compression spring or the like. At least one third elastic member is disposed between the first control segment 320 and gripping portion 310, so that a third spring force from the third elastic member enables relative rotation between the first control segment 320 and gripping portion 310. Or, at least one third elastic member is disposed between the second control segment 330 and gripping portion 310, so that the third spring force from the third elastic member enables relative rotation between the second control segment 330 and gripping portion 310.

Specifically, taking the case that one third elastic member is arranged between the first control segment 320 and gripping portion 310 and another third elastic member is arranged between the second control segment 330 and gripping portion 310 as an example. Due to the third spring force from the third elastic members, the first control segment 320 and gripping portion 310 can be in a relatively open configuration and the second control segment 330 and gripping portion 310 can be in a relatively open configuration. Therefore, the first and second control segments 320, 330 are able to respectively drive the first and second link rods 931, 932 to make the first and second link rods 931, 932 in a relatively open configuration. In use of the surgical instrument 10, each of the first and second control segments 320, 330 approaches the gripping portion 310 through overcoming the third spring forces from the third elastic members, and the first and second control segments 320, 330 respectively drive the first and second link rods 931, 932 to make the first and second link rods 931, 932 in a relatively closed configuration. Further, the first and second link rods 931, 932 drive the transmission shaft 910 to move towards its proximal end, so that the transmission shaft 910 drives the third and fourth link rods 921, 922 to close relatively, which cause relative closing of the first and second jaws 120, 130.

In some embodiments, the opening/closing transmission assembly 900 further includes a fourth elastic member (not shown). The fourth elastic member may be a compression spring or the like. The fourth elastic member is disposed between the first and second jaws 120, 130, so a fourth spring force from the fourth elastic member enables relative rotation between the first and second jaws 120, 130.

Due to the fourth spring force from the fourth elastic member, the first and second jaws 120, 130 can be in a relatively open configuration. In use of the surgical instrument 10, each of the first and second control segments 320, 330 is in a closed configuration through manipulations, and thus the first and second link rods 931, 932 drive the transmission shaft 910. Further, the transmission shaft 910 drives the third and fourth link rods 921, 922 to make the third and fourth link rods 921, 922 in a relatively closed configuration, which causes relative closing of the first and second jaws 120, 130 by overcoming the fourth spring force from the fourth elastic member.

In some embodiments, the surgical instrument 10 further includes a first locking member (not shown). The first locking member may be connected to the spherical hinge 210 and configured to disable or enable the first and second rotational degrees of freedom R1, R2 of the spherical hinge 210. For example, during the operation, there may be a need to observe a sample clamped by the surgical effector assembly 100. In this case, it is required to disable rotation of the surgical effector assembly 100 about the fifth axis and/or sixth axis to help observation of the sample. This can be achieved by locking the first and second rotational degrees of freedom R1, R2 of the spherical hinge 210, so that the spherical hinge 210 is unable to drive the surgical effector assembly 100 to rotate about the fifth axis and/or sixth axis, thereby helping in observing the sample. When the surgical effector assembly 100 is required to again rotate about the fifth axis and/or sixth axis, the first locking member can unlock the first and second rotational degrees of freedom R1, R2 of the spherical hinge 210, so that the spherical hinge 210 can again drive the surgical effector assembly 100 to rotate about the fifth axis and/or sixth axis.

For example, the first locking member may be a snap member, through which the manipulation assembly 300 and/or the first and second rotational degrees of freedom R1, R2 of spherical hinge 210 can be locked.

In some alternative embodiments, the first locking member may be also connected to the manipulation assembly 300 and is configured to lock or unlock driving of the manipulation assembly 300 to the spherical hinge, i.e., locking or unlocking first and second rotational degrees of freedom R1, R2 of the spherical hinge by allowing or disallowing rotation of the spherical hinge about the first and second axes. In this way, the first and second rotational degrees of freedom R1, R2 of the spherical hinge can be disabled by locking driving of the manipulation assembly 300 to the spherical hinge, so that the surgical effector assembly 100 cannot control the manipulation assembly 300 to rotate about the fifth axis and/or sixth axis, thereby facilitating the observation of a sample. Upon a need to again rotate the surgical effector assembly 100 about the fifth axis and/or sixth axis, the first locking member can unlock driving of the manipulation assembly 300 to the spherical hinge, so that the first and second rotational degrees of freedom R1, R2 of the spherical hinge are unlocked and thus the manipulation assembly 300 again controls the surgical effector assembly 100 to rotate about the fifth axis and/or sixth axis.

Figure 9:
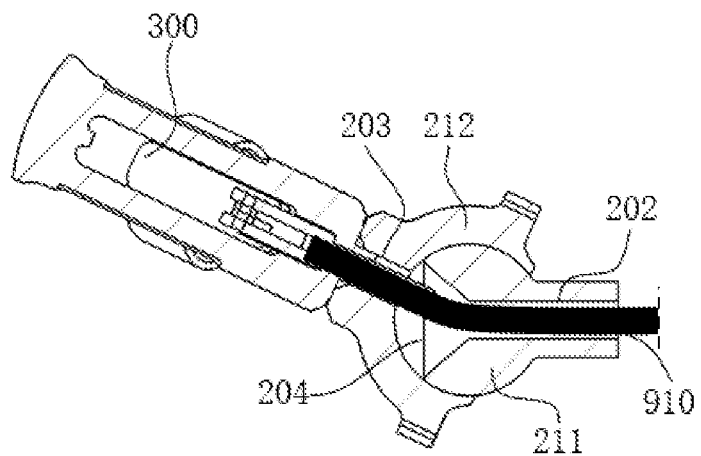
FIG. 9 schematically illustrates a configuration in which the spherical shell of FIG. 1 drives the manipulation assembly to rotate relative to the sphere.
Figure 10:
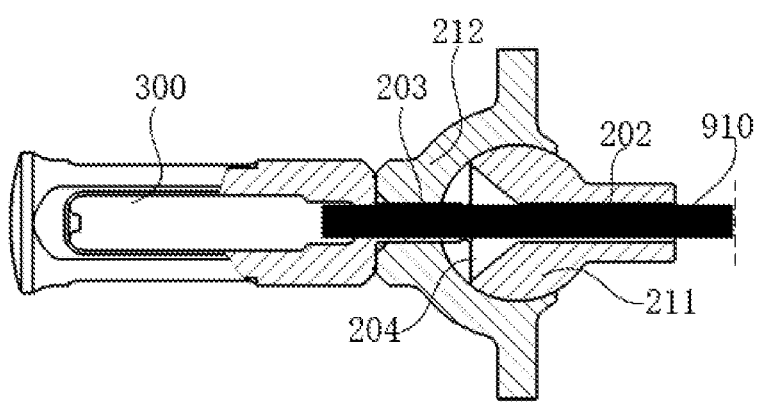
FIG. 10 schematically illustrates another configuration in which the spherical shell of FIG. 1 drives the manipulation assembly to rotate relative to the sphere.

Further, referring to FIG. 9, in some embodiments, the spherical shell 212 is provided with a third passage 203, and the sphere 211 is provided with a fourth passage 202. Referring to FIG. 10, in the initial state, a central axis of the third passage 203 of the spherical shell 212 and a central axis of fourth passage 202 of the sphere 211 are collinear and pass through the common spherical center. Moreover, the third passage 203 of the sphere 211 passes through the extension on the sphere 211. The transmission shaft 910 passes through both the third passage 203 of the spherical shell 212 and the fourth passage 202 of the sphere 211. This arrangement can facilitate the accommodation of the transmission shaft 910 and make a compact structure of the surgical instrument 10.

Further, the spherical shell 212 is arranged between the gripping portion 310 and the sphere 211, and a conical cavity 204 is provided at the proximal end of the sphere 211. The conical cavity 204 is in communication with the fourth passage 202 and has a central axis coinciding with the central axis of the fourth passage 202. When the manipulation assembly 300 drives the spherical shell 212 to rotate about the first or second axis, the portion of the transmission shaft 910 within the conical cavity 204 rotates therein about the common spherical center, without causing movements of the transmission shaft 910 along its extending direction. Thus, the action of the manipulation assembly 300 driving the spherical shell 212 to rotate about the first or second axis does not interfere with movements of the transmission shaft 910 along its extending direction.

In addition, referring to FIG. 9, in some embodiments, the manipulation assembly 300 is also able to self-rotate relative to the spherical shell 212 about the central axis of the third passage 203 to form a third rotational degree of freedom R3, so that the manipulation assembly 300 drives the transmission shaft 910 to self-rotate, which in turn causes the surgical effector assembly 100 to self-rotate under the driving of the transmission shaft 910, and thus forms the seventh rotational degree of freedom R7 of the surgical effector assembly 100.

Further, similar to the first locking member, the surgical instrument further includes a second locking member. The second locking member is connected to the manipulation assembly and configured to allow or disallow rotation of the manipulation assembly about the central axis of third passage 203, so as to enable or disable the third rotational degree of freedom of the manipulation assembly.

In the above embodiments, through the linkage member 200 with two rotational degrees of freedom, when the manipulation assembly 300 drives the surgical effector assembly 100 to rotate in the fifth and/or sixth rotational degree(s) of freedom, the swing directions of the surgical effector assembly 100 in the fifth and/or sixth rotational degree(s) of freedom is in consistent with the swing directions of the manipulation assembly 300 in the first and/or second rotational degree(s) of freedom. Therefore, it provides with an improved directional accuracy of movements of the surgical effector assembly 100, an enhanced action accuracy of the surgical instrument 10 and facilitated surgical operations.

The features of the above-described embodiments may be combined arbitrarily. While not all possible combinations of these features are described for the sake of brevity, they are all considered within the scope of present disclosure as long as there is no contradiction therein.

The above embodiments describe merely a few embodiments of the present disclosure. While the few embodiments have been described specifically and in detail, they are not intended to be understood as limitations to the scope of the disclosure. It is noted that, many variations and modifications can be made by those of ordinary skill in the art without departing from the spirit of the present disclosure, which fall into the protection scope of the the appended claims.

What is claimed is:

1. A surgical instrument, comprising a surgical effector assembly comprising an end effector, a flexible snake assembly, a linkage member, a flexible transmission mechanism, a manipulation assembly and an opening/closing transmission assembly having a distal end connected to the end effector and a proximal end connected to the manipulation assembly, the flexible snake assembly having a distal end connected to the surgical effector assembly and a proximal end connected to a distal end of the linkage member, the linkage member having a proximal end connected to the manipulation assembly, the linkage member being able to rotate about a first axis and a second axis, the flexible snake assembly being able to rotate about a fifth axis and a sixth axis, the flexible transmission mechanism having a proximal end connected to the linkage member and a distal end connected to the flexible snake assembly, wherein a position at which the flexible transmission mechanism is connected to the linkage member and a position at which the flexible transmission mechanism is connected to the flexible snake assembly are arranged in an opposite sequence,
wherein the manipulation assembly comprises a gripping portion and at least one control segment, the at least one control segment having a proximal end rotatably connected to the gripping portion; and the opening/closing transmission assembly comprises a transmission shaft and a first opening/closing coupling part, wherein the first opening/closing coupling part comprising a first link rod having a proximal end rotatably connected to a distal end of the at least one control segment and a distal end connected to the transmission shaft,
wherein a rotation of the at least one control segment relative to the gripping portion drives the first link rod to move, so that the first link rod drives the transmission shaft to move along an extending direction of the transmission shaft,
wherein when the manipulation assembly drives the linkage member to rotate about the first axis, the flexible snake assembly is driven to rotate about the fifth axis, a direction of the rotation of the flexible snake assembly about the fifth axis being the same as a direction of the rotation of the linkage member about the first axis, and
wherein when the manipulation assembly drives the linkage member to rotate about the second axis, the flexible snake assembly is driven to rotate about the sixth axis, a direction of the rotation of the flexible snake assembly about the sixth axis being the same as a direction of the rotation of the linkage member about the second axis.

2. The surgical instrument according to claim 1, wherein the linkage member comprises a spherical hinge, the spherical hinge comprising a sphere and a spherical shell that have a common spherical center, the spherical hinge being restricted from self-rotating about a restricting axis of the spherical shell.

3. The surgical instrument according to claim 2, wherein the linkage member further comprises a limiting pin that is arranged on a surface of the sphere, and has a central axis extending through the common spherical center, the central axis of the limiting pin forming the first axis,
wherein a guiding groove is formed on an inner surface of the spherical shell, an extending direction of which is a circumference direction about the spherical center, the limiting pin received in the guiding groove to cause the limiting pin to be circumferentially movable along the extending direction of the guiding groove, and
wherein the guiding groove has a side wall configured to prevent the limiting pin from rotating about the restricting axis of the spherical shell, an axis about which the limiting pin moves circumferentially along the extending direction of the guiding groove forming the second axis, and
wherein any two of the restricting axis of the spherical shell, the central axis of the limiting pin and the axis about which the limiting pin moves circumferentially along the extending direction of the guiding groove are perpendicular to each other.

4. The surgical instrument according to claim 2, wherein the surgical effector assembly comprises a support portion, the support portion connected to the flexible snake assembly, the end effector being movable relative to the support portion.

5. The surgical instrument according to claim 4, wherein the manipulation assembly causes the end effector to rotate relative to the support portion by means of the opening/closing transmission assembly.

6. The surgical instrument according to claim 4, wherein the end effector comprises a first jaw and a second jaw that are able to rotate relatively, each of the first and second jaws rotatably connected to the support portion.

7. The surgical instrument according to claim 6, wherein the opening/closing transmission assembly further comprises a second opening/closing coupling part having a distal end connected to each of the first and second jaws and a proximal end connected to the transmission shaft, and
wherein when the at least one control segment is rotated relative to a gripping portion of the manipulation assembly, the at least one control segment drives the first opening/closing coupling part to move, which causes the first opening/closing coupling part to drive the transmission shaft to move, so that the transmission shaft drives the second opening/closing coupling part to move, which causes the second opening/closing coupling part to drive the first and second jaws to rotate relative to each other.

8. The surgical instrument according to claim 7, wherein the manipulation assembly comprises a first control segment and a second control segment, the first opening/closing coupling part further comprising a second link rod the second link rod having a proximal end rotatably connected to a distal end of the second control segment and a distal end rotatably connected to the transmission shaft, and
wherein when the first and second control segments rotate relative to each other, the first and second control segments respectively drives the first and second link rods to rotate relative to each other, so that the first and second link rods drives the transmission shaft to move along an extending direction of the transmission shaft.

9. The surgical instrument according to claim 8, wherein the opening/closing transmission assembly further comprises a first elastic member disposed between the first link rod and the second link rod.

10. The surgical instrument according to claim 7, wherein the second opening/closing coupling part comprises a third link rod and a fourth link rod, the third link rod having a distal end rotatably connected to a proximal end of the first jaw, the fourth link rod having a distal end rotatably connected to a proximal end of the second jaw, each of the third and fourth link rods having a proximal end rotatably connected to the transmission shaft, and
wherein when the transmission shaft move towards an extending direction thereof, the transmission shaft drives the third and fourth link rods to rotate relative to each other, so that the third and fourth link rods respectively drives the first and second jaws to rotate relative to each other.

11. The surgical instrument according to claim 10, wherein the opening/closing transmission assembly further comprises a second elastic member disposed between the third and fourth link rods.

12. The surgical instrument according to claim 7, wherein an axis of the spherical shell is provided with a third passage and the sphere is provided with a fourth passage, the third passage having a central axis collinear with a central axis of the fourth passage, the transmission shaft passing through the third and fourth passage, wherein the spherical shell is located between a gripping portion of the manipulation assembly and the sphere that is provided with conical cavity thereon, wherein the conical cavity is in communication with the fourth passage and has a central axis coincident with the central axis of the fourth passage, wherein the conical cavity is arranged at a side of the sphere close to the manipulation assembly.

13. The surgical instrument according to claim 12, wherein the manipulation assembly is rotatable about the central axis of the third passage, so that the manipulation assembly drives the transmission shaft to rotate, which in turn causes the transmission shaft to drive the surgical effector assembly to self-rotate.

14. The surgical instrument according to claim 6, wherein the opening/closing transmission assembly further comprises a fourth elastic member disposed between the first and second jaws.

15. The surgical instrument according to claim 2, wherein the gripping portion is connected to the spherical hinge
wherein the proximal end of the opening/closing transmission assembly is connected to the at least one control segment, so that a rotation of the at least one control segment relative to the gripping portion drives the opening/closing transmission assembly, which in turn drives the end effector to rotate relative to the support portion.

16. The surgical instrument according to claim 15, wherein the opening/closing transmission assembly further comprises at least one third elastic member disposed between the at least one control segment and the gripping portion.

17. The surgical instrument according to claim 1, further comprising a hand-held portion and a connecting portion that are sequentially connected, the hand-held portion having a proximal end connected to the linkage member, the connecting portion having a distal end connected to the flexible snake assembly.

18. The surgical instrument according to claim 17, wherein the hand-held portion comprises an arc-shaped body having a proximal end provided with a proximal holder and a distal end provided with a distal holder, the proximal holder having a distal end fixedly connected to the linkage member, the distal holder having a distal end fixedly connected to the connecting portion.

19. The surgical instrument according to claim 1, further comprising a hand-held portion and a connecting portion that are sequentially connected, the hand-held portion having a proximal end connected to the linkage member, the connecting portion having a distal end connected to the flexible snake assembly, wherein the hand-held is provided with a second passage and connecting portions is provided with a first passage, through which the flexible transmission mechanism passes.

* * * * *